(12) United States Patent
Tao et al.

(10) Patent No.: US 8,795,742 B2
(45) Date of Patent: Aug. 5, 2014

(54) CHINESE TRADITIONAL MEDICINE COMPOSITION FOR TREATMENT OF AVIAN INFLUENZA, METHOD FOR PREPARATION AND APPLICATION THEREOF

(75) Inventors: Desheng Tao, Zhuhai (CN); Yongqing Zeng, Zhuhai (CN); Hui Cao, Zhuhai (CN); Yi Guan, Zhuhai (CN)

(73) Assignee: Livzon Pharmaceutical Group Inc., Zhuhai, Guangdong Province (CN)

( * ) Notice: Subject to any disclaimer, the term of this patent is extended or adjusted under 35 U.S.C. 154(b) by 1097 days.

(21) Appl. No.: 12/030,977

(22) Filed: Feb. 14, 2008

(65) Prior Publication Data

US 2008/0131529 A1 Jun. 5, 2008

Related U.S. Application Data

(63) Continuation of application No. 11/655,563, filed on Jan. 19, 2007, now abandoned.

(30) Foreign Application Priority Data

Jan. 20, 2006 (CN) .......................... 2006 1 0001538

(51) Int. Cl.
*A61K 36/00* (2006.01)
*A61K 36/355* (2006.01)
*A61K 36/489* (2006.01)
*A61K 36/232* (2006.01)

(52) U.S. Cl.
USPC ....................................................... 424/725

(58) Field of Classification Search
None
See application file for complete search history.

(56) References Cited

U.S. PATENT DOCUMENTS

| | | | |
|---|---|---|---|
| 5,009,894 A | 4/1991 | Hsiao | |
| 6,706,293 B1 | 3/2004 | Quintanilla Almagro et al. | |
| 6,790,464 B2 | 9/2004 | Kuok et al. | |
| 2002/0031559 A1 | 3/2002 | Liang et al. | |
| 2003/0143290 A1 | 7/2003 | Cho et al. | |
| 2005/0025841 A1 | 2/2005 | Tze et al. | |
| 2005/0096369 A1 | 5/2005 | Hoang | |
| 2007/0123566 A1 | 5/2007 | Xu et al. | |

FOREIGN PATENT DOCUMENTS

| | | | |
|---|---|---|---|
| CN | 1149469 A | | 5/1997 |
| CN | 1202361 A | | 12/1998 |
| CN | 1265320 A | | 9/2000 |
| CN | 1287840 A | | 3/2001 |
| CN | 1462632 A | * | 12/2003 |
| CN | 1565607 A | * | 1/2005 |
| CN | 1631414 A | | 6/2005 |
| CN | 1682915 A | | 10/2005 |
| CN | 1686239 A | * | 10/2005 |
| HU | 53531 A2 | | 11/1990 |
| JP | 408092109 A | | 4/1996 |

OTHER PUBLICATIONS

USPTO Office Action mailed Apr. 25, 2007 for U.S. Appl. No. 11/655,563.
USPTO Office Action mailed Jun. 27, 2007 for U.S. Appl. No. 11/655,563.
USPTO Office Action mailed Nov. 23, 2007 for U.S. Appl. No. 11/655,563.
USPTO Office Action mailed Jun. 25, 2009 for U.S. Appl. No. 11/030,997.
USPTO Office Action mailed Mar. 30, 2010 for U.S. Appl. No. 12/030,997.
"Guidance for Industry Botanical Drug Products", U.S. Department of Health and Human Services, Food and Drug Administration, Center for Drug Evaluation and Research, Jun. 2004, pp. 3-5 in particular, Section III B, p. 51.
Kou Junping, et al; Abstract: "Preliminary Study on Material Bases of Difference Laxative Potency of Xiao Chengqi-Tang and Other Two Prescriptions", Lishizhen Medicine and Materia Medica Research 10(6): 401-403 (1999) In English and Chinese.
Bupa Health News; Hot topic-Avian flu (bird flu); http://www.bupa.co.uk/health_information/html/health_news/270104avianflue.html, 2009.
TCM Assistant; "Ren Dong Teng" Chinese Herb; http://www.tcmassistant.com/herbs/ren-dong-teng.html, 2009.
Shan Dou Gen, Radix Sophorae Tonkinensis, Sophora tonkinensis Gapnep.Herb Medicine 10419; http://www.alibaba.com/product-gs/207675367/Shan-Dou_Gen_Radix_Sophorae_Tonkinensis.ht, 2009.
Holistic online.com; "Isatis" http://www.holisticonline.com/HerbalMed/_herbs/h358.htm, 2009.

* cited by examiner

*Primary Examiner* — Qiuwen Mi
(74) *Attorney, Agent, or Firm* — Ladas & Parry LLP

(57) ABSTRACT

A Chinese traditional medicine composition for prevention and treatment of avian influenza is provided. Its active ingredients are consisted of: herba houttuyniae 21.4 wt. %, Caulis lonicerae japonicae 17.9 wt. %, radix isatidis 14.3 wt. %, male fern rhizome 10.7 wt. %, radix et rhizoma sophorae tonkinensis 7.1 wt. %, radix angelicae dahuricae 7.1 wt. %, rhizoma paridis 7.1 wt. %, herba artemisiae annuae 7.2 wt. %, and rhizoma iridis tectoris 7.2 wt. %. This Chinese traditional medicine composition could be made into any regular medicinal types, for example, oral solutions, tablets, capsules, pellets and injection solution, etc. Modified preparation methods for this Chinese traditional medicine composition, as well as the use of the same in preparation of medicines and health foods for prevention or treatment of avian influenza were also provided in present invention. This Chinese traditional medicine composition could effectively prevent and treat avian influenza. It was a safer, more easily-obtained, and inexpensive anti-avian influenza drug.

1 Claim, 2 Drawing Sheets

A

B

C

D

CHINESE TRADITIONAL MEDICINE COMPOSITION FOR TREATMENT OF AVIAN INFLUENZA, METHOD FOR PREPARATION AND APPLICATION THEREOF

FIELD OF THE INVENTION

The present invention relates to a Chinese traditional medicine composition for prevention and treatment of Avian Influenza (AI), a method for preparation, and application thereof. More specifically, the present invention relates to a Chinese traditional medicine composition for prevention and treatment of AI that is made from herb, a method for preparing the same, and application thereof.

BACKGROUND OF THE INVENTION

AI is an avian acute contagious symptom caused by type A influenza virus. The affected animals include geese, chickens, ducks, pigeons and some wild birds. The research on contagious diseases has indicated that AIV (Avian Influenza Virus) is highly pathogenic and contagious. AI was defined by World Organization for Animal Health as a type A infection, also known as fowl plague or European plague. There are three types of AI in relation to the pathogen. These include highly pathogenic, low pathogenic and non-pathogenic. No obvious symptoms were caused by non-pathogenic AI. However, some virus antibody was generated in the infected birds. The symptoms caused by low pathogenic AI included marginal respiratory symptom, reduced food intake, reduced egg production, and a few deaths. The highly pathogenic AI could cause the most serious symptoms with a very high death rate. Humans have not yet had effective methods for prevention and treatment of high pathogenic AI, which was found in 1878. Sterilization, separation and flock slaughtering were applied to prevent further spreading. The infected flock had an extremely high death rate which brought serious financial loss.

Naturally, the correlation between AI and human flu happened through intermediate hosts such as pigs, horses, dolphins, and other mammals. However, the antigenic characteristics of the highly pathogenic AIV changed frequently, which was also called antigenic shift and antigenic drift. In addition, its intermediate hosts increased continuously. The highly pathogenic AIV nowadays could infect humans directly. The first case of inter-species infection was in Hong Kong, China, in 1997, and again on China's mainland and Hong Kong in 1999. It was induced by $H_9N_2$ AIV and caused some mortality. It broke the rule in which human and other mammals could only be infected by $H_1$, $H_2$, and $H_3$ influenza virus. $H_5$ and $H_9$ are the newest members of the influenza virus family, which bring new topic for public health. Avian Influenza has broken out in many countries and it has become a major threat to the human health and the safety of global economy.

$H_1$, $H_2$, and $H_3$ were the only influenza virus's found in humans for a long time. All the research, vaccines, and antiviral medications were aimed towards these three viruses. Human beings had neither immunities nor effective medications against the new outbreak of $H_5$, $H_1$, and $H_7$. Serious symptoms, including fever, muscle soreness, and chills, could be caused in humans by highly pathogenic AIV infections. Its complications could even cause death.

The current major medications for anti-influenza virus include neuralminidase inhibitors (such as Zanamivir, Oseltamivir, etc.), ion channel blockers (such as Amantadine and rimantadine), and nucleotide medications (such as tribavirim, that is, ribavirin or virazole). Ion channel blockers were considered as the best medications for prevention and treatment of influenza viruses.

However, the above mentioned medications have shown limitations:

(1) The neuralminidase inhibitors could effectively restrain type A and B influenza viruses. However, it is relatively expensive, which limits its extension. For example, Tamiflu made in Roche Pharmaceutical Corp. was also called Oseltamivirphosphat, i.e., phosphate of Oseltamivir ((3R,4R,5S)-4-acetylamino-5-amino-3(1-ethylpropoxy)-1-cyclohexene-1-carboxylic acid ethyl ester, with CASRN of 196618-13-0) with CASRN of 204255-11-8. This medicine should be taken twice daily with a dosage of 75 mg each time. Thus 60 RMB was needed per day for medicine. 300 RMB was required for one 5-day treatment phase. Furthermore, Roche Pharmaceutical Corp. refused to release the patent for Tamiflu even after 2017, citing justifications such as the complexity of production and maintaining high quality standards. Thus the production of Tamiflu was in short supply.

However, significant side effects have been found with Tamiflu, including hallucinations, abnormal behaviors and other psychological and neural symptoms. Drug resistance has also been observed in some of the patients.

(2) Ion channel blockers could effectively resist type A influenza virus. However, it is poisonous to the nervous system and could induce drug resistance if taken for a long period of time. It also has no effect on type B influenza virus.

(3) Tribavirin (virazole) could effectively treat the infection caused by RNA and DNA viruses. However, this compound has teratogenic effect which limits its application in clinical practices.

In order to find effective and safe treatment for influenza viruses, many scientists turned to Chinese traditional herbs for help. For example, a Chinese traditional medicine composition which could prevent chicken, duck avian influenza, was introduced in article CN200510011432.3 from Huanan Agricultural University. However, this Chinese traditional medicine composition was not very effective in avian influenza treatment, and thus it cannot meet the requirement for inhibiting the outbreak of AI.

Therefore, a safe, effective, inexpensive medicine which could not only prevent but also treat avian influenza is in great need.

SUMMARY OF THE INVENTION

One purpose of the present invention is to provide a Chinese traditional medicine composition for prevention and treatment of avian influenza.

Another purpose of the present invention is to provide a preparation method for the Chinese traditional medicine composition of the present invention.

Yet the other purpose of this invention is to provide uses of the Chinese traditional medicine composition of the present invention in preparation of medicines which are used in prevention and treatment of avian influenza.

A further purpose of this invention is to provide uses of the Chinese traditional medicine composition of the present invention in preparation of health goods which are used in prevention and treatment of avian influenza.

In one embodiment of the present invention, the Chinese traditional medicine composition which could effectively prevent and treat avian influenza comprises active ingredients and/or medical acceptable vector, wherein the active ingredients substantially includes: herba houttuyniae 4.7 wt. %-70.0 wt. %, Caulis lonicerae japonicae 4.7 wt. %-46.7 wt. %, radix isatidis 2.3 wt. %-42.0 wt. %, radix et rhizoma sophorae tonkinensis 1.2 wt. %-35.0 wt. % and other herbs for removing fever and detoxication.

The above mentioned herbs are Male Rern Rhizome, Radix angelicae dahuricae, Herba Andrographic, Dandelion, Natural Indigo, Sargentgloryvine Stem, Chinese Licorice, or the like.

The active ingredients of the above mentioned Chinese traditional medicine composition could also include herba houttuyniae 4.7 wt. %-70.0 wt. %, Caulis lonicerae japonicae 4.7 wt. %-46.7 wt. %, radix isatidis 2.3 wt. %-42.0 wt. %, and radix et rhizoma sophorae tonkinensis 1.2 wt. %-35.0 wt. %.

In another embodiment of the present invention, the Chinese traditional medicine composition which could effectively prevent and treat avian influenza comprises active ingredients and/or medical acceptable vector, wherein the active ingredients substantially includes herba houttuyniae 4.7 wt. %-58.4 wt. %, Caulis lonicerae japonicae 4.7 wt. %-46.7 wt. %, radix isatidis 2.3 wt. %-42.0 wt. %, radix et rhizoma sophorae tonkinensis 1.2 wt. %-35.0 wt. %, male fern rhizome 1.9 wt. %-37.3 wt. %, radix angelicae dahuricae 1.2 wt. %-35.0 wt. %, and other herbs for fever reduction and detoxification.

The above mentioned herbs are rhizoma paridis, herba artemisiae annuae, Java brucea fruit, herba andrographis, dandelion, mint, platycodon grandiflorus, Chinese licorice, or the like.

The active ingredients of the above mentioned Chinese traditional medicine composition could also include herba houttuyniae 4.7 wt. %-58.4 wt. %, Caulis lonicerae japonicae 4.7 wt. %-46.7 wt. %, radix isatidis 2.3 wt. %-42.0 wt. %, radix et rhizoma sophorae tonkinensis 1.2 wt. %-35.0 wt. %, male fern rhizome 1.9 wt. %-37.3 wt. %, and radix angelicae dahuricae 1.2 wt. %-35.0 wt. %.

In another embodiment of the present invention, the Chinese traditional medicine composition which could effectively prevent and treat avian influenza comprises active ingredients and/or medical acceptable vector, wherein the active ingredients is consisted of herba houttuyniae 9.3 wt. %-46.7 wt. %, Caulis lonicerae japonicae 9.3 wt. %-37.3 wt. %, radix isatidis 4.7 wt. %-35.0 wt. %, male fern rhizome 2.3 wt. %-28.0 wt. %, radix et rhizoma sophorae tonkinensis 2.3 wt. %-23.3 wt. %, radix angelicae dahuricae 2.3 wt. %-23.3 wt. %, rhizoma paridis 2.3 wt. %-23.3 wt. %, herba artemisiae annuae 2.3 wt. %-23.3 wt. %, and rhizoma iridis tectoris 2.3 wt. %-23.3 wt. %.

The preferred components of the active ingredients of the above mentioned Chinese traditional medicine composition are herba houttuyniae 14.0 wt. %-35.0 wt. %, Caulis lonicerae japonicae 11.7 wt. %-23.3 wt. %, radix isatidis 9.3 wt. %-21.0 wt. %, male fern rhizome 7.0 wt. %-18.7 wt. %, radix et rhizoma sophorae tonkinensis 4.7 wt. %-11.7 wt. %, radix angelicae dahuricae 4.7 wt. %-11.7 wt. %, rhizoma paridis 4.7 wt. %-11.7 wt. %, herba artemisiae annuae 4.7 wt. %-11.7 wt. %, and rhizoma iridis tectoris 4.7 wt. %-11.7 wt. %.

The more preferred components of the active ingredients of the above mentioned Chinese traditional medicine composition are herba houttuyniae 21.4 wt. %, Caulis lonicerae japonicae 17.9 wt. %, radix isatidis 14.3 wt. %, male fern rhizome 10.7 wt. %, radix et rhizoma sophorae tonkinensis 7.1 wt. %, radix angelicae dahuricae 7.1 wt. %, rhizoma paridis 7.1 wt. %, herba artemisiae annuae 7.2 wt. %, rhizoma iridis tectoris 7.2 wt. %.

The Chinese traditional medicine composition of the present invention could be readily made into any form of drug by conventional methods. For example, the raw materials of the present invention could be ground into powder, mixed and taken with water. The raw materials of the present invention could also be boiled and concentrated into medicines. In order to maximize the effect of all the raw materials, the herba houttuyniae was preferably extracted, for example, by using ethanol. However, these could not be used to limit the scope of the present invention.

The preferred Chinese traditional medicine composition comprises herba houttuyniae, caulis lonicerae japonicae, radix isatidis and male fern rhizome, etc., could be prepared in the following steps:

The above mentioned four herbs were obtained in prescription amounts. The herba houttuyniae was boiled in water for 10~40 minutes. The solution was filtered and concentrated into a clear cream with a density of 1.05-1.20. The cream was then cooled and ethanol was added until the amount of ethanol was 50~80%. It was then allowed to sit for 24-48 hours followed by filtration. The collected ethanol was concentrated and a clear cream of density 1.05-1.25 was obtained. The other three herbs, including caulis lonicerae japonicae, radix isatidis and male fern rhizome, were boiled for 2 hours in water twice. The herbs were filtered and the filtrate was concentrated until a density of 1.40 was reached. Following filtration the obtained filtrate was re-concentrated into a clear cream with a density of 1.45. The herba houttuyniae clear cream was then added and mixed. The mixture was continuously concentrated to thick cream with a density of 1.10 or greater. Finally, the thick cream and powdered sucrose were mixed in a 1:3~8 ratio. The mixture was then made into pellets and packed.

The raw materials in the above mentioned preparation process could also be prepared with male fern rhizome and radix angelicae dahuricae, or with herba androgrraphic, dandelion, natural indigo, sargentgloryvine stem or Chinese licorice. The detailed preparation steps are as follows:

Herba houttuyniae, caulis lonicerae japonicae, radix isatidis, radix et rhizoma sophorae tonkinensis, male fern rhizome and radix angelicae dahuricae were obtained in prescription amount. The herba houttuyniae was boiled in water for 10~40 minutes, filtered, and concentrated into a clear cream with a density of 1.20. The cream was cooled and ethanol was added until the amount of ethanol was 50~80%. It was allowed to sit for 24-48 hours followed by filtration. The ethanol was collected from the filtrate and concentrated to obtain a clear cream with a density of 1.25. The other 5 herbs were boiled in water twice for 2 hours each time. The mixture was then filtered and concentrated to a density of 1.08. Filtered again, the filtrate was concentrated into a clear cream with a density of 1.10, and mixed with the obtained herba houttuyniae clear cream. The mixture was continuously concentrated to obtain a thick cream with a density of 1.26 or above. Finally, the thick cream and powdered sucrose were mixed in a 1:3~8 ratio. The mixture was then made into pellets and packed.

The Chinese traditional medicine composition of the present invention consisting of herba houttuyniae, caulis lonicerae japonicae, radix isatidis, radix et rhizoma sophorae tonkinensis, male fern rhizome, radix angelicae dahuricae, rhizoma paridis, herba artemisiae annuae, and rhizoma iridis tectori, could be prepared in the following steps:

All 9 herbs mentioned above were obtained in prescription amount. The herba houttuyniae was boiled in water for 10~40 minutes, filtered, and concentrated to a clear cream with a density of 1.05. The cream was cooled and ethanol added until the amount of ethanol was 50~80%. It was allowed to sit for 24 hours then filtered. The ethanol was then collected from the filtrate and concentrated to obtain a clear cream with a density of 1.25. The other 8 herbs were boiled in water twice for 2 hours each time. The mixture was then filtered and concentrated to a density of 1.20. Filtered again and the filtrate was concentrated to obtain a clear cream with a density of 1.10-1.25, then mixed with the herba houttuyniae clear cream. The mixture was concentrated to obtain a thick cream with a density of 1.26 or above. Finally, the thick cream and powder sucrose were mixed in a proportion of 1:3~8. The mixture was then made into pellets and packed.

One or more medical acceptable vectors could be added to the Chinese traditional medicine composition of the present invention. For example, regular accessory agents include diluting agents, excipients, fillers, adhesive agents, moisturizing agents, disintegrant agents, absorption enhancers, surfactants, absorbing vectors, lubricants, and the like.

The Chinese traditional medicine composition of the present invention could be taken orally, applied through venous injection or mucous membranes. It could be made into tablets, capsules, powder, pellets, pastille, suppositories, oral solutions, pasteurized gastroenteric suspension injections, small or large amounts of injection, frozen power injections, pasteurized powder injections or the like. All of the above-mentioned medicines could be prepared using regular methods in the art.

In order to treat the infected animals or enhance the animal immunities against avian influenza, the Chinese traditional medicine composition of the present invention could be added to the animal forage as an additive.

The effective application amount of the Chinese traditional medicine composition or additive of the present invention was 20-80 mg/kg body weight per day. The preferred application amount was 30-65 mg/kg body weight per day.

The raw materials of the Chinese traditional medicine composition of the present invention were natural plants. The Chinese traditional medicine composition could significantly resist the avian influenza viruses. The prepared medicines or additives were safe, effective, and provided new methods for prevention and treatment of avian influenza.

BRIEF DESCRIPTION OF THE DRAWINGS

FIG. 1A shows a positive control group without medicine. FIG. 1B shows a control group applied with 0.284 ug/ml of Tamiflu, and a large amount of cells are infected. FIG. 1C shows a control group applied with 2.84 ug/ml of Tamiflu, and most of cells are infected. FIG. 1D shows a control group applied with 28.4 ug/ml of Tamiflu, wherein viruses was killed, but there are many unrelated cells (killed).

FIG. 2A shows a positive control group without medicine. FIG. 2B shows the photograph when applied with 12.5 ug/ml of the Chinese traditional medicine composition of the present invention, and a large amount of cells are infected. FIG. 2C shows photograph when applied with 25 ug/ml of the Chinese traditional medicine composition of the present invention, and a large amount of cells are infected. FIG. 2D shows the photograph when applied with 50 ug/ml of the Chinese traditional medicine composition of the present invention, wherein the viruses are killed, and only a few cells are infected. FIG. 2E shows the photograph when applied with 100 ug/ml of the Chinese traditional medicine composition of the present invention, wherein all viruses are killed, and there are a few unrelated cells (killed). FIG. 2F shows the photograph when applied with 200 ug/ml of the Chinese traditional medicine composition of the present invention, wherein all viruses are killed, but some cells are killed.

DETAIL DESCRIPTION OF EMBODIMENTS OF THE INVENTION

Figure 1:
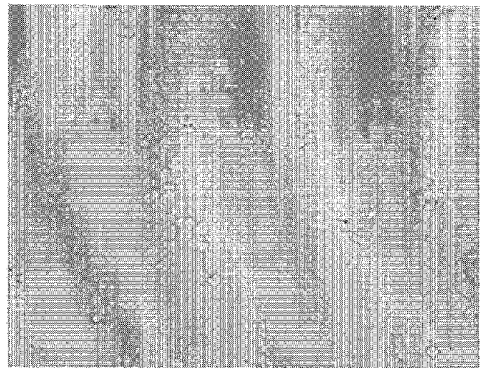
FIG. 1 shows an optical microscopic photograph of the cells of control group in Experiment Example 3, while the culture of cells was stopped.
Figure 1:
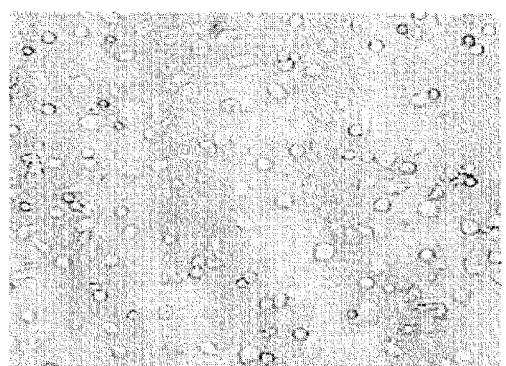
Figure 1:
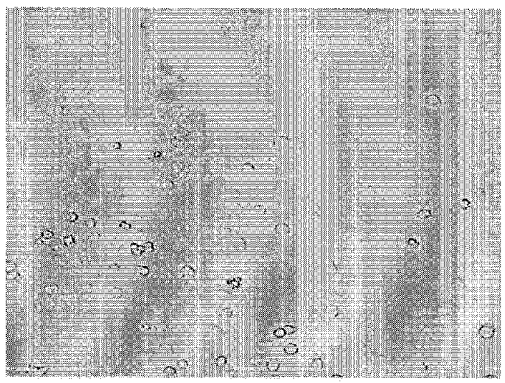
Figure 1:
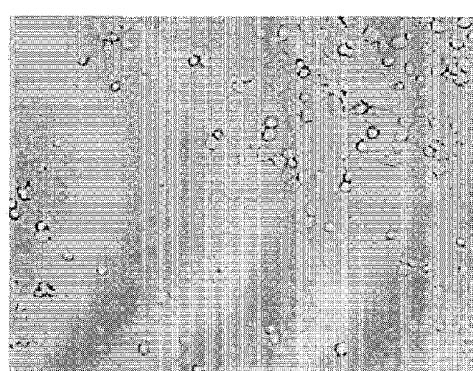
Figure 2:
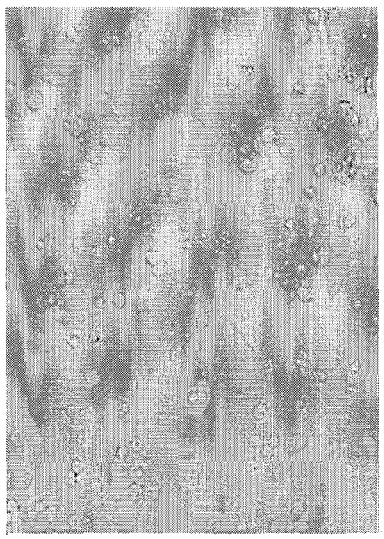
FIG. 2 shows optical microscopic photograph of the cells of control group in Experiment Example 3, while the culture of cells was stopped.
Figure 2:
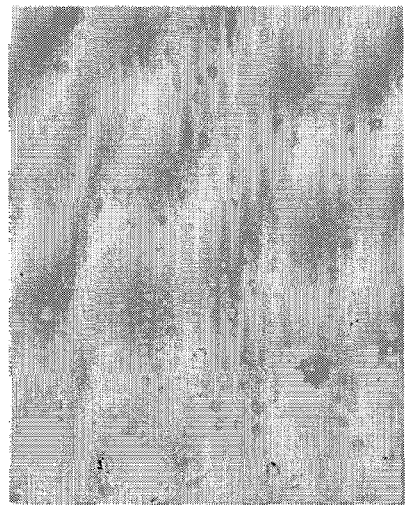
Figure 2:
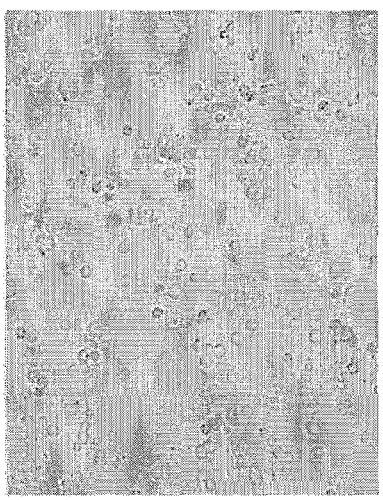
Figure 2:
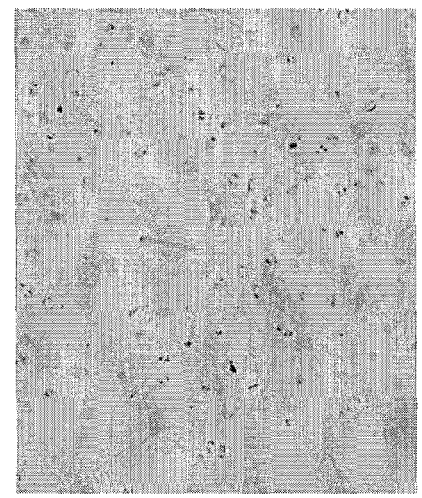
Figure 2:
Figure 2:
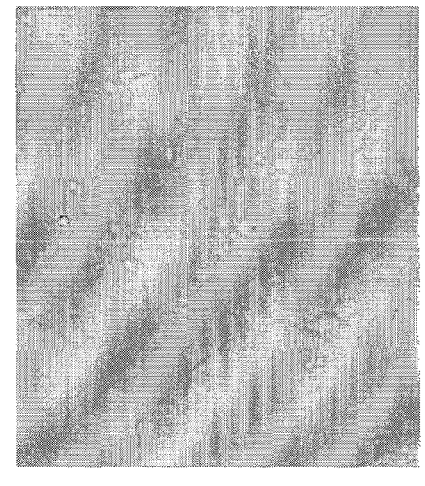

The following Experiment Examples is to further describe the benefit of the Chinese traditional medicine composition of the present invention over the current existing anti-avian influenza medicines. The following Experiment Example includes the cytological and zoological experiments for the Chinese traditional medicine composition of the present invention.

Experiment Example 1

The protective effect of the Chinese traditional medicine composition of the present invention for the flocks infected with avian influenza viruses.

The chickens used in this experiment were healthy 50-day old yellow chicken, which were purchased from the experimental chicken farm of Zhongshan University. The Chinese traditional medicine composition of the present invention (which is the pellet in Example 5), was provided by the Lizhu Pharmaceutical Group, Inc. The Rimantadine, one of the control medicines, was purchased from Zhejiang Yukang Pharmaceutical Corp. The other control medicine was prepared according to China Patent 200510011432.3. The virus was H5 serum type avian influenza virus ($1.0 \times 10^{-6}$).

Experimental Process:

190 healthy yellow chickens of 50-days old were randomly grouped into 5 groups. 30 were in the normal control group, the other groups have 40 yellow chickens each. Each chicken was injected in the abdomen with 0.2 ml of avian influenza virus diluted in chicken embryo amniotic fluid with a concentration of $0.5 \times 10^{-5}$. Each group was fed with medicine the same day infected with AIV, except the healthy control group and infected control group, which were fed with physiological saline. The medicine or physiological saline was applied once per day continuously for 8 days. Group A was the healthy control group. Group B was applied with 10 mg/day the Chinese traditional medicine composition of the present invention. Group C was applied with 10 mg/day Rimantadine, one of the control medicines. Group D was applied with 10 mg/day of the medicine prepared according to China Patent 200510011432.3. Group E was the infected control group. The results are shown in the following table 1:

TABLE 1

| Group | Number | Treatment method | Number of death | Rate of death | Effective rate |
|---|---|---|---|---|---|
| A | 30 | Not infected | 0 | — | — |
| B | 40 | Infected, medicine applied | 1 | 2.5% | 97.5% |
| C | 40 | Infected, medicine applied | 23 | 57.5% | 42.5% |
| D | 40 | Infected, medicine applied | 16 | 40% | 60% |
| E | 40 | Infected, medicine not applied | 37 | 92.5% | — |

The above table shows that the infected chickens were much more effectively protected by the Chinese traditional medicine composition of the present invention than medicine of China Patent 200510011432.3 and Rimantadine.

Experiment Example 2

This was an experiment for treatment of viral pneumonia caused by $H_7$ avian influenza virus.

The lab animals were the Kunming mice provided by the experimental animal lab of Haerbing Medical University. The mice were injected with $H_5N_1$ viruses. The Chinese traditional medicine composition injections in this experiment were provided by the Lizhu Pharmaceutical Group, Inc.

Experimental Process:

Each of the experimental groups and control groups had 17 mice. Control group 1 was injected in the abdomen with 15 ml/kg of physiological saline. Control group 2 was injected in the abdomen with 15 ml/kg of Zedoray Tumeric Oil injection. Control group 3 was injected in the abdomen with 15 ml/kg of ShuangSuLian injection which was often used in the treatment of pneumonia. Experimental group 1 was injected in the abdomen with 15 ml/kg of injection solution which was made from houttuyniae, caulis lonicerae japonicae, radix isatidis and male fern rhizome. Experimental group 2 was injected in the abdomen with 15 ml/kg of injection solution which was made from houttuyniae, caulis lonicerac japonicae, radix isatidis, male fern rhizome, and Chinese licorice. Experimental group 3 was injected in the abdomen with 15 ml/kg of injection solution which was made from houttuyniae, caulis lonicerae japonicae, radix isatidis, male fern rhizome, tokin sophora root, and radix angelicae dahuricae. All medicines were applied continuously for 10 days. Mice in all groups were killed after 11 days and samples were collected for testing. The results are shown in Table 2:

TABLE 2

| Group | Significant effective | effective | Not effective | Death |
|---|---|---|---|---|
| Experimental group 1 | 9 | 4 | 4 | 3 |
| Experimental group 2 | 8 | 3 | 6 | 5 |
| Experimental group 3 | 12 | 4 | 1 | 2 |
| Control group 1 | 0 | 2 | 15 | 13 |
| Control group 2 | 3 | 5 | 9 | 8 |
| Control group 3 | 2 | 3 | 12 | 10 |

Note:
"Significantly effective" means the symptoms were greatly relieved, including normal body temperature and a greatly reduced lung vesicular breath sound.
"Effective" means the symptoms were relieved, including normal body temperature and slightly reduced lung vesicular breath sound.
"Not effective" means the symptoms were not relieved at all or more severe.

Table 2 shows that the Chinese traditional medicine composition used in experimental groups 1, 2, and 3 had a much more positive effect compared to control groups 1, 2, and 3. The Chinese traditional medicine composition significantly improved lung circulation, reduced aggregation of blood platelets, reduced lung infection, healed lung damage, and resisted $H_7$ avian influenza virus. The Chinese traditional medicine composition in Experimental group 3 showed a much more positive effect than in control groups 1 and 2.

Experiment Example 3

This experiment was the in vitro cytological research on the resistance of the Chinese traditional medicine composition of the present invention against highly pathogenic AI.

The medicines used in this experiment were the pellets made in Example 7. The control medicine was Tamiflu, that is, Oseltamivir phosphate made by Roche Corp. The cells used in this experiment were MDCK cells (dog kidney cells), which were provided by the Microbiology Department of Medicine Faculty of the University of Hong Kong. The virus used in this experiment was $H_5N_1$ (geno type E), which was also provided by the Microbiology Department of Medicine Faculty of the University of Hong Kong.

Experimental Process:
(1) Cell toxicity test: the medicine concentration ($CC_{50}$) which induced pathological changes in 50% of the cells was tested according Mosmann rules (1983).
(2) Anti-virus test: a certain amount of viral suspension was put into bottles containing cell cultures. 8 bottles were placed parallel for 45 minutes to let the viruses attach to the cells. Cultural solutions lacking or with differing concentrations of medicines were put into the bottles. The solutions were incubated at 37° C. for 20 hours. The cultures were terminated when 50% of the cells showed pathological changes in the bottle with respect to control cells. Photographs were taken. The results are shown in Table 3:

TABLE 3

| Medicine | Virus | Concentration of the medicine (ug/ml) | |
|---|---|---|---|
| Experimental group | H5N1(genotype E) | 12.5 | +8/8 |
| Experimental group | H5N1(genotype E) | 25 | +8/8 |
| Experimental group | H5N1(genotype E) | 50 | +2/8 |
| Experimental group | H5N1(genotype E) | 100 | +0/8 |
| Experimental group | H5N1(genotype E) | 200 | +0/8 |
| Positive control group | | | |
| Tamiflu | H5N1(genotype E) | 0.284 | +8/8 |
| Tamiflu | H5N1(genotype E) | 2.84 | +2/8 |
| Tamiflu | H5N1(genotype E) | 28.4 | +0/8 |

Note:
+ means non-resistance, negative control cells were normal cells.

Table 3 shows that the Chinese traditional medicine composition injection solution could effectively resist the avian influenza virus when the concentration of the active ingredients was 50 ug/ml or above.

The preparation methods of the Chinese traditional medicine composition of the present invention are described as follows:

Example 1

Preparation of Large Volume Injections of the Chinese Traditional Medicine Composition of the Present Invention First, the following herbs were obtained: 2000 g of herba houttuyniae, 400 g of caulis lonicerae japonicae, 1500 g of radix isatidis, 284 g of male fern rhizome, 100 g of radix et rhizoma sophorae tonkinensis, 100 g of radix angelicae dahuricae, 100 g rhizoma paridis, 100 g of herba artemisiae annuae, and 100 g of rhizoma iridis tectori. The herbs were added with 8× water, soaked for 3 hours, then boiled and extracted twice for 1 hour each time. The extracts were combined, filtered, and concentrated under vacuum to a density of 1.25 at 65° C. They were then cooled and mixed with ethanol until 70%, then allowed to sit. The supernatant was collected, and the ethanol was removed from the liquid. The obtained solution was then concentrated to a density of 1.15 at 65° C. and counter-current extracted using 2× ethyl acetate. The extracts were combined and the ethyl acetate was removed. 50% of the injection water was added. The liquid was then boiled, cooled, and filtered, followed by mixing with suitable amount of injection water. The solution was then mixed with 0.08% of emulsifier (T-80) followed by addition of 40% of NaOH until a pH of 8.0 was reached. NaCl was added to the solution followed by injection water to obtain the isotonic solution. At last, the liquid was filtered through 0.22 µm microvoid filter film, sealed, pasteurized, lamp-inspected, and packed.

Example 2

Preparation of Small Volume Injections of the Chinese Traditional Medicine Composition of the Present Invention First, the following herbs were obtained: 400 g of herba houttuyniae, 1600 g of caulis lonicerae japonicae, 200 g of radix isatidis, 100 g of male fern rhizome, 1000 g of radix et rhizoma sophorae tonkinensis, 200 g of radix angelicae dahuricae, 200 g rhizoma paridis, 384 g of herba artemisiae annuae, and 200 g of rhizoma iridis tectori. All herbs were boiled, filtered, concentrated in a vacuum chamber, added to ethanol, allowed to sit, filtered and concentrated under vacuum until 9 g medicine/ml were obtained. The solution was diluted in water, stored in a fridge, filtered, concentrated under vacuum, and separated in a macroporous resin which was washed with water, NaOH solution, 35 wt % of ethanol, and 75 wt % of ethanol. The eluate was collected, diluted with water, combined with L-Arginase, adjusted until a pH 7.5 was reached, followed by addition of active carbon. The eluate was then heated, filtered, diluted in the same volume of water, followed by addition of L-Arginase until a concentration of 4 wt % was reached.

Example 3

Preparation of Frozen-Dry Powder Injections of the Chinese Traditional Medicine Composition of the Present Invention First, the following herbs were obtained: 584 g of herba houttuyniae, 500 g of caulis lonicerae japonicae, 400 g of radix isatidis, 300 g of male fern rhizome, 500 g of radix et rhizoma sophorae tonkinensis, 500 g of radix angelicae dahuricae, 500 g rhizoma paridis, 500 g of herba artemisiae annuae, and 500 g of rhizoma iridis tectori. All herbs were added to 3200 ml of injection water, soaked for 1 hour, added to 6400 ml of injection water, boiled twice for 1.5 hours each time, and filtered. The filtrate was combined and the extract composition was obtained. 10 g of the extract composition was diluted in injection water, and then added to 2.25 g of NaCl followed by injection water until a volume of 250 ml was reached. Injection carbon was added and the solution was boiled for 20 minutes, cooled, filtered, and pasteurized. The final frozen powder injection was then packed in low-boro glass ampoules, cooled, and dried.

Example 4

Preparation of Small Volume Injections of the Chinese Traditional Medicine Composition of the Present Invention First, the following herbs were obtained: 200 g of herba houttuyniae, 200 g of caulis lonicerae japonicae, 100 g of radix isatidis, 1279 g of male fern rhizome, 1500 g of radix et rhizoma sophorae tonkinensis, and 1500 g of radix angelicae dahuricae. All herbs were added to water, boiled, and filtered. The mixture was concentrated under vacuum, added to ethanol, allowed to sit, then filtered again. The mixture was again concentrated under vacuum until 11 g medicine/ml was obtained. The medicine was diluted in water, stored in a fridge, filtered a third time, concentrated under vacuum, and separated in macroporous resin which was washed with water, NaOH solution, 55 wt % of ethanol, and 65 wt % of ethanol. The eluate was collected, diluted, added L-Arginase, adjusted until a pH 7.0 was reached, added active carbon, heated, and filtered. The final product was obtained by diluting of the eluate with the same volume of water.

Example 5

Preparation of Pellets of the Chinese Traditional Medicine Composition of the Present Invention First, the following herbs were obtained: 2500 g of herba houttuyniae, 1000 g of caulis lonicerae japonicae, 400 g of radix isatidis, 784 g of male fern rhizome, 50 g of radix et rhizoma sophorae tonkinensis, and 50 g of radix angelicae dahuricae. All herbs were added to 70 wt. % of ethanol, soaked overnight, refluxed to extract twice for 1.5 hours each time, and filtered. The residue I and solution I were collected. The residue I was put into a vacuum concentrating pot, and recovered under vacuum until no more ethanol remained, and concentrated into a thick cream.

Starch was dried, sieved. Mannitol was sieved, and allowed to sit. 500 g of the thick cream was mixed with 500 g mannitol and 150 g starch. The mixture was then made into pellets on the granulator with steel mesh, dried on an ebullated bed, modified with 8 mesh screener, tested for content and water, packed with 7 g per bag, sealed and stored in a cool dry place.

Example 6

Preparation of Tablets of the Chinese Traditional Medicine Composition of the Present Invention First, the following herbs were obtained: 3000 g of herba houttuyniae, 1134 g of caulis lonicerae japonicae, 100 g of radix isatidis, and 50 g of radix et rhizoma sophorae tonkinensis. All herbs were added with 3200 ml injection water, soaked for 1 hour, added with 3200 ml injection water again, boiled twice with 1 hour each time, and filtered. The residues were discarded. The solution was put in triple effect evaporator and concentrated until a density of 1.08 (70° C.) was reached, and cooled to room temperature. 95% ethanol was added slowly until the concentration of ethanol was 50%, and allowed to sit overnight. The supernatant was collected and the precipitates were discarded. The supernatant was concentrated and mixed with 200 g filler. The mixture was then put in the granulator, added 60 ml of 30 wt. % ethanol, formed into pellets, and dried.

Second, 50 g of vitamins were mixed with 120 g of filler. The mixture was put into the granulator, added 35 ml of 6 wt. % adhesive, formed into pellets, and dried.

Third, the above two types of pellets were mixed in prescription proportion, tested, formed into tablets in a 33 rotary type tablet presser, and packed.

Example 7

Preparation of Pellets of the Chinese Traditional Medicine Composition of the Present Invention First, the following herbs were obtained: 918 g of herba houttuyniae, 765 g of caulis lonicerae japonicae, 612 g of radix isatidis, 459 g of male fern rhizome, 306 g of radix et rhizoma sophorae tonkinensis, 306 g of radix angelicae dahuricae, 306 g rhizoma paridis, 306 g of herba artemisiae annuae, and 306 g of rhizoma iridis tectori. The herba houttuyniae was boiled in water for 40 minutes, filtered, concentrated to a clear cream with a density of 1.05, cooled, added with ethanol until the amount of ethanol was 80%, sat for 48 hours, and filtered again. Ethanol was recovered from the filtrate, concentrated to a clear cream with a density of 1.05. The rest of the 8 herbs were boiled in water twice for 2 hours each time and filtered. The filtrate was concentrated to a clear cream with a density of 1.08, filtered and concentrated to a density of 1.10. Then, the two clear creams were mixed together and concentrated continuously until a thick cream with a density of 1.26 or above was obtained. The thick cream and powder sucrose were mixed in a proportion of 1:5, formed into pellets, and packed.

Example 8

Preparation of Capsules of the Chinese Traditional Medicine Composition of the Present Invention First, the following herbs were obtained: 200 g of herba houttuyniae, 500 g of caulis lonicerac japonicae, 384 g of radix isatidis, 800 g of male fern rhizome, 200 g of radix et rhizoma sophorae tonkinensis, 200 g of radix angelicae dahuricae, 1000 g rhizoma paridis, 1000 g of herba artemisiae annuae, and 200 g of rhizoma iridis tectori. All the herbs were added to 3200 ml of injection water, soaked for 1 hour, mixed with 7200 ml of injection water, boiled twice for 1 hour each time, and filtered. The filtrates were combined, recovered under vacuum until no more ethanol remained, concentrated into a thick cream with a density of 1.0 (tested at 60° C.). The cream was put in a vacuum drier, dried at 70° C. under vacuum for 36 hours, then crushed and sieved in 60-80 mesh. The medicine powder was then mixed with accessory agents, sieved again, and made into pellets. The pellets were dried, sieved in 20 mesh, mixed with magnesium stearate, and made into capsules.

Example 9

Preparation of Capsules of the Chinese Traditional Medicine Composition of the Present Invention First, the following herbs were obtained: 600 g of herba houttuyniae, 2000 g of caulis lonicerae japonicae, 1200 g of radix isatidis, and 484 g of radix et rhizoma sophorae tonkinensis. All the herbs were added to 3200 ml of injection water, soaked for 1 hour, mixed with 3200 ml of injection water, boiled twice for 2.5 hours each time, and filtered. The filtrates were combined, recovered under vacuum until no more ethanol remained, and concentrated into a thick cream with a density of 1.30. The cream was put in a vacuum drier, dried at 80° C. under vacuum for 48-96 hours, then crushed and sieved in 60-80 mesh. The medicine powder was then mixed with accessory agents, sieved again in 60 mesh, and formed into pellets. The pellets were then dried, sieved in 20 mesh, mixed with magnesium stearate, and made into capsules.

Example 10

Preparation of Milk Products (Health Foods) of the Chinese Traditional Medicine Composition of the Present Invention First, the following herbs were obtained: 200 g of herba houttuyniae, 2000 g of caulis lonicerae japonicae, 584 g of radix isatidis, and 1500 g of radix et rhizoma sophorae tonkinensis. All the herbs were added to 3200 ml of injection water, soaked for 1 hour, mixed with 3200 ml of injection water, boiled twice with 2.5 hours each time, and filtered. The filtrates were combined, recovered under vacuum until no more ethanol remained, concentrated into a thick cream with a density of 1.08.

The cow's milk was tested, pasteurized and preprocessed according to standard (not for skim milk). 0.5-6 mg of the above concentration of solution was added to every 100 g of milk. This was then added with certain flavor. The milk mixtures were filtered, preheated (≤115° C.), pasteurized, homogenized (not for skim milk), cooled, added with yeasts (canned first if it would solidify), and allowed to ferment. The solidified, fermented milk was then crushed (not for solidifying type), cooled, canned (not for solidifying type), and tested to obtain the final product.

Example 11

Preparation of Drinks (Food) of the Chinese Traditional Medicine Composition of the Present Invention First, the following herbs were obtained: 600 g of herba houttuyniae, 1000 g of caulis lonicerae japonicae, 1800 g of radix isatidis, 80 g of male fern rhizome, and 404 g of radix et rhizoma sophorae tonkinensis, 200 g of radix angelicae dahuricae, 100 g of dandelion, and 100 g of herba andrographics. All herbs were thoroughly washed, crushed, and added to base solution containing 2%-3% of NaOH (based on the weight of drug) and 0.3% of sodium hexametaphosphate (based on the weight of drug). The solution was heated at 85° C. for 5 minutes and washed in running water until neutral. Second, the medicine was cut in thick flakes, made into a thick liquid in an electrical liquefier, allowed to sit in a stainless steel container, combined with 2% edible phosphate, then heated in an 75° C. water bath for 70 minutes with constant stirring. Third, the thick liquid was neutralized with edible sodium bicarbonate, while the liquid was cooled in water bath with constant stirring. The fluid was then filtered, pressed and dried. Fourth, the filtrate was added with 6% of powder active carbon, incubated in an 88° C. water bath for 120 minutes, and filtered. Slightly yellow or brown filtrate was obtained. The filtrate was then pasteurized, packed and mixed with hydrolyzed medicine, phosphate, and citrate in a proportion of 100:3:4. The medicine was added with water in a proportion of 1:50. Finally the medicine was mixed, packed in bottles, sealed and pasteurized.

Example 12

Preparation of Medicine of Chinese Traditional Medicine Composition of the Present Invention for Animals First, the following herbs were obtained: 400 g of herba houttuyniae, 400 g of caulis lonicerae japonicae, 200 g of radix isatidis, 100 g of male fern rhizome, and 1000 g of radix et rhizoma sophorae tonkinensis, 1000 g of radix angelicae dahuricae, 1000 g of rhizoma paridis, 1000 g of herba artemisiae annuae, and 1000 g of rhizoma iridis tectori. All herbs were crushed, filtered through 80 mesh, mixed, and packed.

Example 13

Preparation of Vaccines of the Chinese Traditional Medicine Composition of the Present Invention First, the following herbs were obtained: 1500 g of herba houttuyniae, 400 g of caulis lonicerae japonicae, 584 g of radix isatidis, 800 g of male fern rhizome, and 500 g of radix et rhizoma sophorae tonkinensis, and 500 g of radix angelicae dahuricae. All herbs were boiled in water and filtered. The filtrate was concentrated under vacuum, combined with ethanol, filtered, and concentrated again under vacuum to a density of 11 g drug/ml. The solution was diluted in water, stored in a fridge, filtered, concentrated a third time under vacuum, and separated in macroporous resin which was washed subsequently with water, NaOH, and 55 wt % ethanol. The medicine was washed using 65 wt % ethanol. The eluate was collected, diluted in water, combined with L-Arginase, adjusted to a pH of 7.0, combined with active carbon, and filtered. The final vaccine was obtained by mixing the same volume of the filtrate with physiological saline.

Example 14

Preparation of Capsules of the Chinese Traditional Medicine Composition of the Present Invention First, the following herbs were obtained: 2000 g of herba houttuyniae, 200 g of caulis lonicerae japonicae, 400 g of radix isatidis, 900 g of radix et rhizoma sophorae tonkinensis, and 784 g of radix angelicae dahuricae All herbs were soaked in 3200 ml of water for 1 hour, boiled in 3200 ml of injection water twice for 2.5 hours each time, and filtered. The filtrate was then combined, recollected under vacuum until no more ethanol remained, and concentrated into a thick cream with a density of 1.30. The cream was dried in a vacuum oven at 80° C. for 48-96 hours, crushed, and filtered through 60-80 mesh. The powder medicine was mixed with accessory agent, filtered through 60 mesh, formed into pellets, dried, combined with magnesium stearate, and made into capsules.

Example 15

Preparation of Preventive Injections of the Chinese Traditional Medicine Composition of the Present Invention First, the following herbs were obtained: 484 g of herba houttuyniae, 500 g of caulis lonicerae japonicae, 1800 g of radix isatidis, and 1500 g of radix et rhizoma sophorae tonkinensis. All herbs were boiled in water, filtered, concentrated under vacuum, combined with ethanol, and filtered again. The filtrate was concentrated under vacuum to a density of 11 g drug/ml, diluted in water, stored in a fridge, filtered, and concentrated a third time under vacuum. The concentrate was separated in macroporous resin which was washed subsequently with water, NaOH, and 55 wt % ethanol. The medicine was washed off using 65 wt % ethanol. The eluate was collected, diluted in water, combined with L-Arginase, adjusted to a pH of 7.0, combined with active carbon, and filtered. The final drug was obtained by mixing the same volume of the filtrate with physiological saline.

Example 16

Preparation of Capsules of the Chinese Traditional Medicine Composition of the Present Invention First, the following herbs were obtained: 1600 g of herba houttuyniae, 800 g of caulis lonicerae japonicae, 800 g of radix isatidis, 600 g of radix et rhizoma sophorae tonkinensis, and 484 g of herba andrographis. All herbs were soaked in 3200 ml of injection water for 1 hour, boiled in 3200 ml of injection water twice for 2.5 hours each time, and filtered. The filtrate was then combined, recovered under vacuum until no ethanol remained, and concentrated to a thick cream with a density of 1.30. The cream was dried in vacuum oven at 80° C. for 48-96 hours, crushed, and filtered through 60-80 mesh. The powder medicine was mixed with an accessory agent, filtered through 60 mesh, made into pellets, dried, combined with magnesium stearate, and made into capsules.

Example 17

Preparation of Capsules of the Chinese Traditional Medicine Composition of the Present Invention First, the following herbs were obtained: 1700 g of herba houttuyniae, 1000 g of caulis lonicerac japonicae, 400 g of radix isatidis, 500 g of radix et rhizoma sophorae tonkinensis, and 684 g of Java Brucea Fruit. All herbs were soaked in 3200 ml of injection water for 1 hour, boiled in 3200 ml of injection water twice for 2.5 hours each time, and filtered. The filtrate was then combined, recovered under vacuum until no more ethanol remained, and concentrated into a thick cream with a density of 1.20. The cream was dried in vacuum oven at 80° C. for 48-96 hours, crushed, and filtered through 60-80 mesh. The powder medicine was mixed with accessory agents, filtered through 60 mesh, formed into pellets, dried, combined with magnesium stearate, and made into capsules.

Example 18

Preparation of Capsules of the Chinese Traditional Medicine Composition of the Present Invention First, the following herbs were obtained: 1500 g of herba houttuyniae, 1000 g of caulis lonicerae japonicae, 100 g of radix isatidis, 800 g of male fern rhizome, 500 g of radix et rhizoma sophorae tonkinensis, and 384 g of radix angelicae dahuricae. All herbs were soaked in 3200 ml of injection water for 1 hour, boiled in 7200 ml of injection water twice for 1 hour each time, and filtered. The filtrate was then combined, recovered under vacuum until no ethanol remained, and concentrated into a thick cream to a density of 1.0 (tested at 60° C.). The cream was dried in a vacuum oven at 70° C. for 36 hours, crushed, and filtered through 60-80 mesh. The powder medicine was mixed with accessory agents, filtered through 20 mesh, formed into pellets, dried, combined with magnesium stearate, and made into capsules.

Example 19

Preparation of Syrup of the Chinese Traditional Medicine Composition of the Present Invention First, the following herbs were obtained: 200 g of herba houttuyniae, 200 g of caulis lonicerac japonicae, 1800 g of radix isatidis, and 1500 g of radix et rhizoma sophorae tonkinensis. Naphtha was extracted from the herbs by steam. The herbs were then boiled in 6~8 times of their volume of water for 3 times, 1 hour each time. The solution was combined, filtered, concentrated under vacuum (40° C.), and precipitated at low temperature for 24 hours. The supernatant was combined with naphtha, Syrupus Simplex, preservation (sodium benzoate), and distilled water until 1000 ml. The solution was mixed, packed and pasteurized in flowing steam for 30 minutes.

What is claimed is:

1. A method of preparing a Chinese traditional medicine composition for treatment of Avian Influenza comprising active ingredients and medical acceptable vectors, wherein said active ingredients consisting of the following raw materials: herba houttuyniae 9.3 wt. %-46.7 wt. %, caulis lonicerae japonicae 9.3 wt. %-37.3 wt. %, radix isatidis 4.7 wt. %-35.0 wt., male fern rhizome 2.3 wt. %-28.0 wt. %, radix et rhizoma sophorae tonkinensis 2.3 wt. %-23.3 wt. %, radix anaelicae dahuricae 2.3 wt. %-23.3 wt. %, rhizoma paridis 2.3 wt. %-23.3 wt. %, herba artemisiae annuae 2.3 wt. %-23.3 wt. %, rhizoma iridis tectoris 2.3 wt. %-23.3 wt. %, wherein the method comprises the steps of:

1) all raw materials are weighed;

(2) the herba houttuyniae is boiled in water for 10~40 minutes, and filtered, then the filtrate is concentrated to obtain a clear cream with a density of 1.05, and cooled;

(3) the clear cream from step 2 is added with ethanol until the amount of ethanol is 50~80%, allowed to sit for 24 hours and filtered, then ethanol is recovered from the filtrate and the filtrate is concentrated to obtain a clear cream with a density of 1.25;

(4) other raw materials are boiled in water twice for 2 hours each time and filtered, then the filtrate is concentrated to a density of 1.20, filtered, and concentrated again to obtain a clear cream with a density of 1.10-1.25;

(5) the clear cream from step 3 and step 4 are mixed, concentrated continuously to obtain a thick cream with a density of 1.26 or above, and added with accessory agents.

* * * * *